US010966964B2

United States Patent
Lu et al.

(10) Patent No.: US 10,966,964 B2
(45) Date of Patent: *Apr. 6, 2021

(54) METHOD FOR PREPARING PHARMACEUTICAL COMPOSITION COMPRISING PYRROLO-FUSED SIX-MEMBERED HETEROCYCLIC COMPOUND

(71) Applicant: Jiangsu Hengrui Medicine Co., Ltd., Jiangsu (CN)

(72) Inventors: Yun Lu, Jiangsu (CN); Xinhua Zhang, Jiangsu (CN); Chenyang Wang, Jiangsu (CN); Tonghui Liu, Jiangsu (CN)

(73) Assignee: Jiangsu Hengrui Medicine Co., Ltd., Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/080,086

(22) PCT Filed: Feb. 28, 2017

(86) PCT No.: PCT/CN2017/075113
§ 371 (c)(1),
(2) Date: Aug. 27, 2018

(87) PCT Pub. No.: WO2017/148361
PCT Pub. Date: Sep. 8, 2017

(65) Prior Publication Data
US 2019/0060290 A1 Feb. 28, 2019

(30) Foreign Application Priority Data
Mar. 1, 2016 (CN) .......................... 201610115984.7

(51) Int. Cl.
| | | |
|---|---|---|
| A61K 31/437 | (2006.01) | |
| A61K 9/20 | (2006.01) | |
| A61K 9/16 | (2006.01) | |
| A61K 47/26 | (2006.01) | |
| A61K 9/50 | (2006.01) | |
| A61K 47/02 | (2006.01) | |
| A61K 47/12 | (2006.01) | |
| A61K 47/36 | (2006.01) | |
| A61K 47/44 | (2017.01) | |
| A61P 35/00 | (2006.01) | |
| A61P 35/04 | (2006.01) | |

(52) U.S. Cl.
CPC .......... *A61K 31/437* (2013.01); *A61K 9/1623* (2013.01); *A61K 9/2018* (2013.01); *A61K 9/2077* (2013.01); *A61K 9/5089* (2013.01); *A61K 47/02* (2013.01); *A61K 47/12* (2013.01); *A61K 47/26* (2013.01); *A61K 47/36* (2013.01); *A61K 47/44* (2013.01); *A61P 35/00* (2018.01); *A61P 35/04* (2018.01)

(58) Field of Classification Search
CPC .. A61K 31/437; A61K 9/2018; A61K 9/1623; A61K 9/2077; A61K 9/5089; A61K 47/02; A61K 47/12; A61K 47/36; A61K 47/44; A61K 47/26; A61P 35/00; A61P 35/04
See application file for complete search history.

(56) References Cited

U.S. PATENT DOCUMENTS

| | | | |
|---|---|---|---|
| 2009/0136570 A1* | 5/2009 | Rege ..................... | A61K 9/2095 424/465 |
| 2013/0338131 A1* | 12/2013 | Staric .................. | A61K 9/2018 514/210.02 |

FOREIGN PATENT DOCUMENTS

| | | |
|---|---|---|
| CN | 101007814 A | 8/2007 |
| WO | 2007085188 A1 | 8/2007 |

OTHER PUBLICATIONS

Sandler, Niklas, and Robert Frank Lammens. "Pneumatic dry granulation: potential to improve roller compaction technology in drug manufacture." Expert opinion on drug delivery 8.2 (2011): 225-236.*
"Chinese Pharmacopoeia," 2015 Edition, vol. IV, edited by National Pharmacopoeia Commission, China Medical Science and Technology Press, pp. 121-122, English Translation.*
"Chinese Pharmacopoeia," 2015 Edition, vol. IV, edited by National Pharmacopoeia Commission, China Medical Science and Technology Press, pp. 121-122.
Int'l Search Report dated Jun. 8, 2017 in Int'l Application No. PCT/CN2017/075113.
Liu et al, "Clinical Efficacy of Famitinib Malate for Treatment of Metastatic Renal Cell Carcinoma—a Report of 9 Cases," Academic Journal of Second Military Medical University, vol. 36, No. 12, pp. 1348-1351 (Dec. 2015).
Pharmaceutics (Second Edition), edited by the Pharmaceutical Research Group of Nanjing Pharmaceutical University, People's Medical Publishing I-louse, 1985, pp. 1081-1082.

\* cited by examiner

*Primary Examiner* — John Pak
*Assistant Examiner* — Daniel L Branson
(74) *Attorney, Agent, or Firm* — Ice Miller LLP

(57) ABSTRACT

The present invention provides a method for preparing a pharmaceutical composition containing a pyrrolo-fused six-membered heterocyclic compound or a pharmaceutically acceptable salt thereof. Specifically, the invention provides a preparation method of a pharmaceutical composition, the method containing: mixing 5-(2-diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one or a pharmaceutically acceptable salt thereof with at least one filler, and then granulating the mixture. The pharmaceutical composition of the invention features a rapid dissolution and good stability.

13 Claims, 1 Drawing Sheet

METHOD FOR PREPARING PHARMACEUTICAL COMPOSITION COMPRISING PYRROLO-FUSED SIX-MEMBERED HETEROCYCLIC COMPOUND

CROSS-REFERENCE TO RELATED APPLICATIONS

This application is a Section 371 of International Application No. PCT/CN2017/075113, filed Feb. 28, 2017, which was published in the Chinese language on Sep. 8, 2017, under International Publication No. WO 2017/148361 A1, which claims priority under 35 U.S.C. § 119(b) to Chinese Application No. 201610115984.7, filed Mar. 1, 2016, the disclosures of which are incorporated herein by reference in their entirety.

FIELD OF THE INVENTION

The present invention belongs to the field of pharmaceutical formulations. Specifically, the present invention relates to a method for preparing a pharmaceutical composition comprising 5-(2-diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one or a pharmaceutically acceptable salt thereof.

BACKGROUND OF THE INVENTION

With the development of molecular biology technology and further understanding of the pathogenesis of tumors from the molecular level of cellular receptors and proliferation regulation, therapy targeting cell receptors, key genes, and regulatory molecules begins to enter the clinic, which is called "molecular targeted therapy". These fields include targeted epidermal growth factor receptor (EGFR) blockers, monoclonal antibodies targeting certain specific cell markers, drugs targeting certain oncogenes and cytogenetic markers of cancers, anti-tumor angiogenesis drugs, anti-tumor vaccines, and gene therapies etc.

The antitumor mechanism of tyrosine kinase inhibitors (TKIs) that first entered the clinic can be achieved by the following ways: inhibiting injury repair of tumor cells, blocking cell division in the G1 phase, inducing and maintaining cell apoptosis, and anti-neovascularization, etc. Overexpression of EGFR often indicates poor prognosis, rapid metastasis, resistance to chemotherapeutic drugs, resistance to hormones, and shorter life span, etc., in patients. TKIs can also inhibit the "cross-talk" between the two signaling transduction pathways of EGFR and vascular endothelial growth factor receptor (VEGFR) by down-regulating the angiogenic factor in tumor cells and inhibiting the signaling transduction of EGFR on tumor vascular endothelial cells. It provides a reasonable basis for clinical inhibition of both transduction pathways simultaneously. Results of clinical trials show that multi-target inhibitors are superior to single-target inhibitors in terms of treatment. Multi-targets in combination with blocking of signaling transduction is a new direction for tumor therapy and drug development.

Up to now, the FDA has approved multiple multi-target TKIs, such as sorafenib, vandetanib, and Sunitinib (Sutent, SU-11248). Among them, Sunitinib was approved in January 2006 for treating GIST and advanced kidney cancer. Since there are currently no drugs for the treatment of advanced GIST in the clinic except for imatinib, and there are few drugs for kidney cancer, the results of Sunitinib are encouraging. WO2007085188 discloses a compound similar to Sunitinib, as shown in formula (I) below, which can be better applied to the treatment of the above tumors. The chemical name of the compound is 5-(2-diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one. It is known to inhibit tumor proliferation and angiogenesis, and selectively inhibit the kinase activity of vascular endothelial growth factor (VEGF) receptor. It can be used clinically for the treatment of various tumors such as kidney cancer, gastrointestinal stromal tumor, colorectal cancer, and pancreatic neuroendocrine tumor, etc.

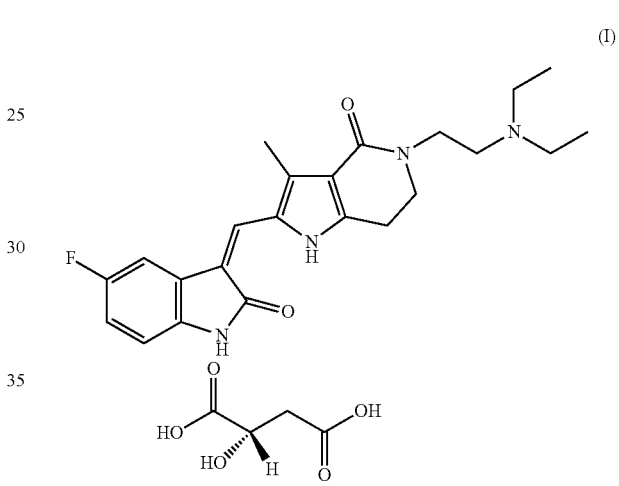

Since the compound of formula (I) or a pharmaceutically acceptable salt thereof has poor water solubility, and is unstable in the presence of moisture, water cannot be used as a solvent for wet granulation. When the compound of formula (I) or a pharmaceutically acceptable salt thereof is formulated into a pharmaceutical composition by using a conventional preparation method, the resulting composition is difficult to dissolve rapidly and keep its quality stable. There is a need to find a suitable method to obtain a stable composition with a rapid dissolution.

BRIEF SUMMARY OF THE INVENTION

The object of the present invention is to provide a method for preparing a pharmaceutical composition with a good stability and rapid dissolution. The preparation method has simple process and is suitable for large-scale production.

The method for preparing a pharmaceutical composition according to the present invention comprises mixing the active ingredient with at least one filler, followed by granulating the mixture. The active ingredient is 5-(2-diethyl-amino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one or a pharmaceutically acceptable salt thereof.

The granulation method can be selected from the group consisting of high shear wet granulation, wet one-step granulation, and dry granulation, preferably dry granulation. The filler can be present in an amount of 20%-95%, preferably 30%-90%, more preferably 40%-85%, and most preferably 50%-80% by weight, relative to the total weight of the composition.

It is surprisingly found in the present invention that the dissolution of the composition obtained by mixing the active ingredient with a filler, followed by granulating the mixture is much better than that of the composition obtained by directly mixing the active ingredient with a filler, followed by filling the mixture into capsules or tableting it into tablets. The dissolution of the composition without granulation cannot meet the requirement.

Due to the process of mixing the active ingredient with a filler, followed by granulating the mixture, the dissolution of the pharmaceutical composition of the present invention is good. The dissolution rate is determined according to the second method of general rule 0931 of volume IV of Chinese Pharmacopoeia 2015 Edition, using purified water (preferably 900 ml) as a dissolution medium at 37±0.5° C. and at a paddle speed of 50 rpm. The dissolution rate is greater than or equal to 80% in 45 minutes.

The water-soluble filler can be a sugar alcohol, preferably one or more of lactose, glucose, sucrose, mannitol, and sorbitol.

In a preferred embodiment of the present invention, the water-soluble filler is mannitol.

The above water-soluble filler is in close contact with the active ingredient during the granulation process, which can promote the dissolution of the active ingredient and keep its stability. The content of the water-soluble filler of the present invention is not particularly limited. In a preferred embodiment of the present invention, the water-soluble filler can be present in an amount of 20%-95%, preferably 30%-90%, more preferably 40%-85%, and most preferably 50%-80% by weight, relative to the total weight of the composition.

The pharmaceutical composition of the present invention has good stability. The degradation product is less than or equal to 0.5% after the composition has been placed at a temperature of 25° C. and relative humidity of 75% for 10 days, or the degradation product is less than or equal to 1% after the composition has been placed at a temperature of 25° C. and relative humidity of 90% for 10 days. When the above water-soluble filler is used, the pharmaceutical composition has good stability. However, when other fillers are used, the stability may become poor.

In the pharmaceutical composition of the present invention, the pharmaceutically acceptable salt of the active ingredient can be selected from the group consisting of hydrochloride, malate, hydrobromide, p-toluenesulfonate, methanesulfonate, sulfate, and ethanesulfonate, preferably malate. The active ingredient can be present in an amount of 3%-40%, preferably 5%-30%, and most preferably 10%-20% by weight, relative to the total weight of the composition.

The pharmaceutical composition according to the present invention can comprise other fillers, for example, one or more of starch, pregelatinized starch, dextrin, ormicrocrystalline cellulose, etc. The other fillers are present in an amount of about 5-50 wt %, relative to the total weight of the composition.

The pharmaceutical composition according to the present invention can comprise a disintegrant, wherein the disintegrant is one or more selected from the group consisting of croscarmellose sodium, sodium carboxymethyl starch, low substituted hydroxypropyl cellulose and crospovidone. The disintegrant is preferably present in an amount of about 1%-20% by weight, relative to the total weight of the composition.

The pharmaceutical composition according to the present invention can further comprise one or more lubricant(s) that facilitates capsule filling or tableting. The lubricant can be selected from the group consisting of talc, magnesium stearate, sodium stearyl fumarate, zinc stearate, glyceryl behenate, sodium lauryl sulfate, hydrogenated vegetable oil, and colloidal silicon dioxide, etc. The lubricant is preferably present in an amount of about 0.5%-5% by weight, relative to the total weight of the composition.

In a particularly preferred embodiment of the present invention, the method for preparing a pharmaceutical composition comprises the following steps of:

mixing 10-20 wt % of 5-(2-diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one or a pharmaceutically acceptable salt thereof with 30-80 wt % of lactose or mannitol, followed by dry granulating the mixture, tableting the resulting granules into tablets or filling them into capsules; wherein the particle size distribution range d(0.9) of the active ingredient is preferably less than 60 μm, and most preferably less than 40 μm; and the composition further comprises:

1) optionally 5-50 wt % of pregelatinized starch;

2) 1-30 wt % of a disintegrant, wherein the disintegrant is one or more selected from the group consisting of croscarmellose sodium, sodium carboxymethyl starch, low substituted hydroxypropyl cellulose and crospovidone; and 3) 0.5-5 wt % of a lubricant, wherein the lubricant is one or more selected from the group consisting of magnesium stearate, sodium stearyl fumarate, colloidal silicon dioxide, and talc.

The method for preparing the pharmaceutical composition of the present invention further comprises a step of tableting the dry granules into tablets or filling them into capsules. The pharmaceutical composition of the present invention is preferably prepared into hard capsules.

When the particle size distribution of the active ingredient of the pharmaceutical composition of the present invention meets a certain requirement, it can promote more rapid dissolution of the composition. The particle size of the active ingredient is determined by a laser particle size analyzer. d(0.9) should be less than 100 μm, preferably less than 80 μm, more preferably less than 60 μm, and most preferably less than 40 μm.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
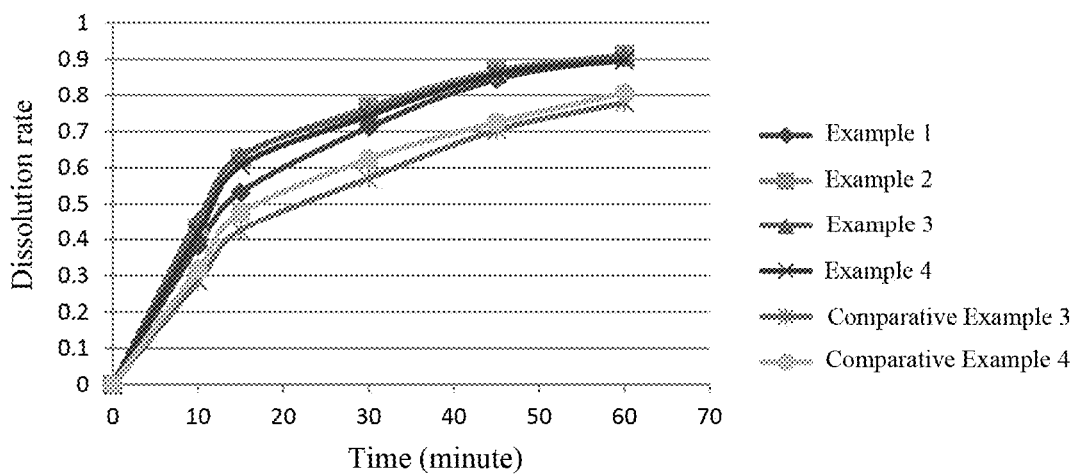
FIG. 1 shows the dissolution profiles of the capsules of Examples 1 to 4 and Comparative Examples 3 and 4 in purified water.

The present invention is further described in detail by the following examples and experimental examples. These examples and experimental examples are for illustrative purposes only, and are not intended to limit the scope of the present invention.

EXAMPLES 1-4, COMPARATIVE EXAMPLES 1-4

5-(2-Diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one malate (hereinafter referred to as compound A), pregelatinized starch, lactose, crospovidone, and silicon dioxide were mixed well according to the prescription ratios of Examples 1-4 shown in Table 1. Dry granulation was carried out by a dry granulator, and a prescription amount of magnesium stearate was then added and mixed well with the granules. The resulting total mixed granules were filled into capsules to prepare the capsules.

Compound A, microcrystalline cellulose, crospovidone, and silicon dioxide were mixed well with calcium hydrophosphate or pregelatinized starch according to the prescription ratios of Comparative Examples 1 and 2 shown in Table 1. Dry granulation was carried out by a dry granulator, and a prescription amount of magnesium stearate was then added and mixed well with the granules. The resulting total mixed granules were filled into capsules to prepare the capsules.

Compound A, pregelatinized starch, lactose, crospovidone, silicon dioxide, and magnesium stearate were mixed well according to the prescription ratio of Comparative Example 3 shown in Table 1. The resulting mixed powder was filled into capsules to prepare the capsules.

Compound A, lactose, crospovidone, silicon dioxide, and magnesium stearate were mixed well according to the prescription ratio of Comparative Example 4 shown in Table 1. The resulting mixed powder was filled into capsules to prepare the capsules.

TABLE 1

| Ingredients | Example 1 | Example 2 | Example 3 | Example 4 | Comparative Example 1 | Comparative Example 2 | Comparative Example 3 | Comparative Example 4 |
| --- | --- | --- | --- | --- | --- | --- | --- | --- |
| Compound A | 22.1 | 13.3 | 8.8 | 13.3 | 13.3 | 13.3 | 13.3 | 8.8 |
| Microcrystalline cellulose | 0 | 0 | 0 | 0 | 50.3 | 50.3 | 0 | 0 |
| Calcium hydrophosphate | 0 | 0 | 0 | 0 | 0 | 30.0 | 0 | 0 |
| Pregelatinized starch | 33.3 | 15.0 | 0 | 30.0 | 30.3 | 0 | 15.0 | 0 |
| Lactose | 38.1 | 67.3 | 86.7 | 50.3 | 0 | 0 | 67.3 | 86.7 |
| Crospovidone | 5.0 | 3.0 | 3.0 | 5.0 | 5.0 | 5.0 | 3.0 | 3.0 |
| Silicon dioxide | 0.5 | 0.5 | 0.5 | 0.5 | 0.5 | 0.5 | 0.5 | 0.5 |
| Magnesium stearate | 1.0 | 1.0 | 1.0 | 1.0 | 1.0 | 1.0 | 1.0 | 1.0 |
| Total | 100 | 100 | 100 | 100 | 100 | 100 | 100 | 100 |

Unit: weight %

EXAMPLES 5-8, COMPARATIVE EXAMPLES 5-8

Compound A, pregelatinized starch, mannitol, crospovidone, and silicon dioxide were mixed well according to the prescription ratios of Examples 5-8 shown in Table 2. Dry granulation was carried out by a dry granulator, and a prescription amount of magnesium stearate was then added and mixed well with the granules. The resulting total mixed granules were filled into capsules to prepare the capsules of Examples 5-8.

Compound A, pregelatinized starch, calcium hydrophosphate, crospovidone, and silicon dioxide were mixed well according to the prescription ratio of Comparative Example 5 shown in Table 2. Dry granulation was carried out by a dry granulator, and a prescription amount of magnesium stearate was then added and mixed well with the granules. The resulting total mixed granules were filled into capsules to prepare the capsules of Comparative Example 5.

Compound A, pregelatinized starch, mannitol, crospovidone, silicon dioxide, and magnesium stearate were mixed well according to the prescription ratio of Comparative Example 6 shown in Table 2. The resulting mixed powder was filled into capsules to prepare the capsules of Comparative Example 6.

Compound A, mannitol, crospovidone, silicon dioxide, and magnesium stearate were mixed well according to the prescription ratio of Comparative Example 7 shown in Table 2. The resulting mixed powder was filled into capsules to prepare the capsules of Comparative Example 7. Compound A, pregelatinized starch, mannitol, and crospovidone were mixed well according to the prescription ratio of Comparative Example 8 shown in Table 2. Anhydrous ethanol was then added, and wet granulation was carried out. The granules were dried and milled. Silicon dioxide and magnesium stearate were added and mixed well with the granules. The resulting mixture was filled into capsules to prepare the capsules of Comparative Example 8.

results show that in the capsules of Examples 1-8 which were prepared by a dry granulation process, the dissolution of compound A is rapid; whereas in the capsules of Comparative Examples 3-4 and 6-8 which were not prepared by a dry granulation process, the dissolution of compound A is slow and incomplete.

Figure 2:
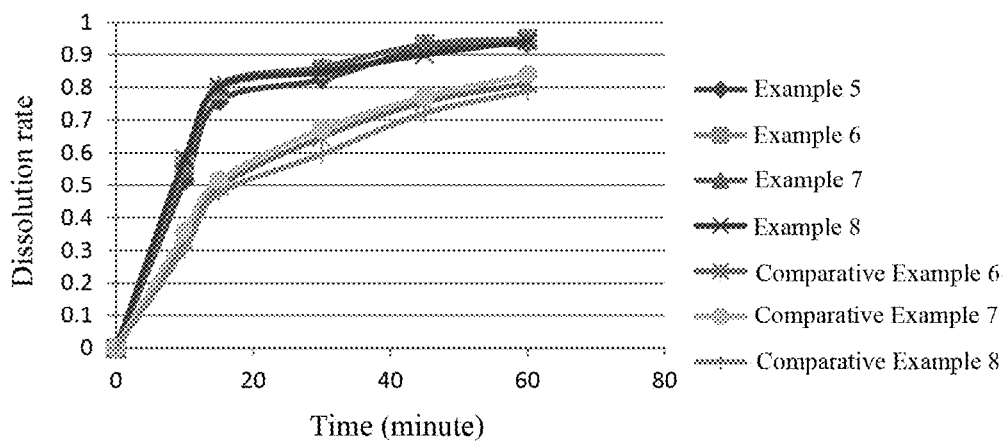
FIG. 2 shows the dissolution profiles of the capsules of Examples 5 to 8 and Comparative Examples 6 to 8 in purified water.

The dissolution profiles are shown in FIGS. 1 and 2.

EXAMPLES 9-11, COMPARATIVE EXAMPLE 9

Compound A of Examples 9-11 and Comparative Example 9 with different particle sizes shown in Table 3, respectively, were mixed well with pregelatinized starch, mannitol, crospovidone, and silicon dioxide according to the prescription ratio of Example 6 shown in Table 2. Dry granulation was carried out by a dry granulator, and a prescription amount of magnesium stearate was then added and mixed well with the granules. The resulting total mixed granules were filled into capsules to prepare the capsules of Examples 9-11 and Comparative Example 9.

TABLE 3

| Samples | Comparative Example 9 | Example 9 | Example 10 | Example 11 |
|---|---|---|---|---|
| Particle size distribution d0.9 of compound A | 128 μm | 67 μm | 55 μm | 37 μm |

Note: The Particle size distribution of compound A shown in Table 3 is determined by a Malvern Laser Particle Size Analyzer Mastersizer2000. The refractive index of the particles is 1.520. The injector is Scirocco2000 (A), the analysis mode is universal (fine powder), and the sensitivity is normal.

TABLE 2

| Ingredients | Example 5 | Example 6 | Example 7 | Example 8 | Comparative Example 5 | Comparative Example 6 | Comparative Example 7 | Comparative Example 8 |
|---|---|---|---|---|---|---|---|---|
| Compound A | 22.1 | 13.3 | 8.8 | 13.3 | 13.3 | 13.3 | 8.8 | 13.3 |
| Calcium hydrophosphate | 0 | 0 | 0 | 0 | 50.3 | 0 | 0 | 0 |
| Pregelatinized starch | 33.3 | 15.0 | 0 | 30.0 | 30.0 | 15.0 | 0 | 15.0 |
| Mannitol | 38.1 | 67.3 | 86.7 | 50.3 | 0 | 67.3 | 86.7 | 67.3 |
| Crospovidone | 5.0 | 3.0 | 3.0 | 5.0 | 5.0 | 3.0 | 3.0 | 3.0 |
| Silicon dioxide | 0.5 | 0.5 | 0.5 | 0.5 | 0.5 | 0.5 | 0.5 | 0.5 |
| Magnesium stearate | 1.0 | 1.0 | 1.0 | 1.0 | 1.0 | 1.0 | 1.0 | 1.0 |
| Total | 100 | 100 | 100 | 100 | 100 | 100 | 100 | 100 |

Unit: weight %

EXPERIMENTAL EXAMPLE 1

Dissolution Test

The dissolution rates of the capsules of Examples 1-8 and Comparative Examples 3, 4, 6, 7 and 8 were determined according to the dissolution and release test (the second method of general rule 0931 of volume IV of Chinese Pharmacopoeia 2015 Edition). The dissolution test was carried out using 900 ml of purified water as a dissolution medium at 37±0.5° C. and at a paddle speed of 50 rpm. The

EXPERIMENTAL EXAMPLE 2

Dissolution Test

The dissolution rates of the capsules of Examples 9-11 and Comparative Example 9 were determined according to the dissolution and release test (the second method of general rule 0931 of volume IV of Chinese Pharmacopoeia 2015 Edition). The dissolution test was carried out using 900 ml of purified water as a dissolution medium at 37±0.5° C. and at a paddle speed of 50 rpm. The results show that in the capsules of Examples 9-11, as the particle size distribution d0.9 of compound A whose particle size distribution d0.9 is lower than 100 μm becomes smaller, the dissolution rates of the capsules become gradually faster, indicating that the smaller the particle size distribution d0.9 of compound A is, the faster the capsules dissolve. However, the particle size of compound A of Comparative Example 9 is more than 100 μm, and the dissolution thereof is slow.

Figure 3:
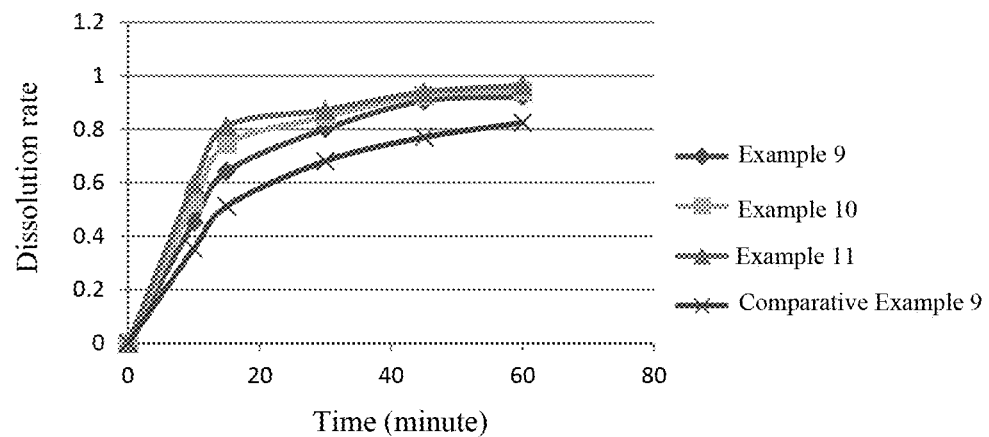
FIG. 3 shows the dissolution profiles of the capsules of Examples 9 to 11 and Comparative Example 9 in purified water.

The dissolution profiles are shown in FIG. 3.

EXPERIMENTAL EXAMPLE 3

Stability Test

The capsules of Examples 4 and 6, and the capsules of Comparative Examples 1, 2 and 5 were respectively placed under open conditions at a temperature of 25° C. and relative humidity of 75%, or at a temperature of 25° C. and relative humidity of 90% for 5 days and 10 days, and then the degradation products were determined by a HPLC method. The results show that in a high-humidity environment, the growth rates of the degradation products of Examples 4 and 6, which comprise lactose or mannitol, are significantly lower than that of Comparative Examples 1, 2 and 5, which do not comprise lactose and mannitol, indicating that the capsules comprising lactose or mannitol are more stable in a high-humidity environment. The results of the test are shown in Table 4.

TABLE 4

| Samples | Degradation product (%) at a temperature of 25° C. and relative humidity of 75% | | | Degradation product (%) at a temperature of 25° C. and relative humidity of 90% | | |
| --- | --- | --- | --- | --- | --- | --- |
| | Initial state | Placed for 5 days | Placed for 10 days | Initial state | Placed for 5 days | Placed for 10 days |
| Example 4 | 0.16 | 0.20 | 0.39 | 0.16 | 0.64 | 0.91 |
| Example 6 | 0.17 | 0.18 | 0.32 | 0.17 | 0.59 | 0.79 |
| Comparative Example 1 | 0.19 | 0.38 | 0.61 | 0.19 | 0.92 | 1.63 |
| Comparative Example 2 | 0.20 | 0.41 | 0.69 | 0.20 | 1.05 | 1.81 |
| Comparative Example 5 | 0.17 | 0.32 | 0.55 | 0.17 | 0.86 | 1.49 |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for preparing a pharmaceutical composition, comprising:
   1) mixing together by weight of the total pharmaceutical composition:
      a) 10-20 wt % of 5-(2-diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one or a pharmaceutically acceptable salt thereof,
      b) 30-80 wt % of lactose or mannitol;
      c) 5-50 wt % of pregelatinized starch;
      d) 1-30 wt % of a disintegrant, wherein the disintegrant is at least one selected from the group consisting of croscarmellose sodium, sodium carboxymethyl starch, low substituted hydroxypropyl cellulose and crospovidone; and
      e) 0.5-5 wt % of a lubricant, wherein the lubricant is at least one selected from the group consisting of magnesium stearate, sodium stearyl fumarate, colloidal silicon dioxide, and talc to form a mixture;
   2) dry granulating the mixture to form dry granules; and
   3) tableting the dry granules into tablets or filling the dry granules into capsules,
   wherein the 5-(2-diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one or the pharmaceutically acceptable salt thereof has a particle size distribution range d(0.9) of less than 60 μm.

2. The method for preparing the pharmaceutical composition according to claim 1, wherein the composition has a dissolution rate greater than or equal to 80% in 45 minutes, wherein the dissolution rate is determined according to the second method of general rule 0931 of volume IV of Chinese Pharmacopoeia 2015 Edition, and wherein the method uses purified water as a dissolution medium at 37±0.5° C. and at a paddle speed of 50 rpm.

3. The method for preparing the pharmaceutical composition according to claim 1, wherein the mannose or lactose is present in an amount of 50%-80% by weight, relative to the total weight of the composition.

4. The method for preparing the pharmaceutical composition according to claim 1, wherein the disintegrant is crospovidone.

5. The method for preparing the pharmaceutical composition according to claim 1, wherein the lubricant is magnesium stearate, colloidal silicon dioxide or a combination thereof.

6. The method for preparing the pharmaceutical composition according to claim 1, wherein the pharmaceutically acceptable salt is selected from the group consisting of hydrochloride, malate, hydrobromide, p-toluenesulfonate, methanesulfonate, sulfate, and ethanesulfonate.

7. The method for preparing the pharmaceutical composition according to claim 1, wherein the 5-(2-diethylamino-ethyl)-2-(5-fluoro-2-oxo-1,2-dihydro-indol-3-ylidene-methyl)-3-methyl-1,5,6,7-tetrahydro-pyrrolo[3,2-c]pyridin-4-one or the pharmaceutically acceptable salt thereof is present in an amount of 13.3%-20% by weight, relative to the total weight of the composition.

8. The method for preparing the pharmaceutical composition according to claim 1, wherein the pharmaceutical composition is a tablet.

9. The method for preparing the pharmaceutical composition according to claim 1, wherein the pharmaceutical composition is a capsule.

10. The method for preparing the pharmaceutical composition according to claim 1, wherein the particle size distribution range d(0.9) is less than 40 μm.

11. The method for preparing the pharmaceutical composition according to claim 1, wherein the disintegrant is present in an amount of 1-20% by weight, relative to the total weight of the composition.

12. The method for preparing the pharmaceutical composition according to claim 1, wherein the lubricant is present in an amount of 1.5% by weight, relative to the total weight of the composition.

13. The method for preparing the pharmaceutical composition according to claim 1, wherein the pharmaceutically acceptable salt is malate.

* * * * *